(12) United States Patent
Koseoglu et al.

(10) Patent No.: US 9,778,240 B2
(45) Date of Patent: Oct. 3, 2017

(54) CHARACTERIZATION OF CRUDE OIL BY ULTRAVIOLET VISIBLE SPECTROSCOPY

(75) Inventors: Omer Refa Koseoglu, Dhahran (SA); Adnan Al-Hajji, Dammam (SA); Gordon Jamieson, London (GB)

(73) Assignee: Saudi Arabian Oil Company, Dhahran (SA)

( * ) Notice: Subject to any disclaimer, the term of this patent is extended or adjusted under 35 U.S.C. 154(b) by 1406 days.

(21) Appl. No.: 13/400,787

(22) Filed: Feb. 21, 2012

(65) Prior Publication Data

US 2015/0106034 A1   Apr. 16, 2015

Related U.S. Application Data

(60) Provisional application No. 61/445,217, filed on Feb. 22, 2011.

(51) Int. Cl.
  *G01N 21/64* (2006.01)
  *G01N 33/28* (2006.01)
  *G01N 21/33* (2006.01)

(52) U.S. Cl.
  CPC ......... *G01N 33/2823* (2013.01); *G01N 21/33* (2013.01)

(58) Field of Classification Search
  CPC ............................................ G06K 19/06112
  USPC ............................................ 250/461.1, 255
  See application file for complete search history.

(56) References Cited

U.S. PATENT DOCUMENTS

| | | |
|---|---|---|
| 3,896,312 A | 7/1975 | Brown |
| 4,988,446 A | 1/1991 | Haberman |
| 5,121,337 A | 6/1992 | Brown |
| 5,266,800 A | 11/1993 | Mullins |
| 5,304,807 A | 4/1994 | Lin |
| 5,424,959 A | 6/1995 | Reyes |
| 5,475,612 A | 12/1995 | Espinosa |
| 5,656,810 A | 8/1997 | Alfano |
| 6,490,029 B1 | 12/2002 | Cho |
| 6,633,043 B2 * | 10/2003 | Hegazi ............... G01N 21/6408 250/458.1 |
| 6,662,116 B2 | 12/2003 | Brown |
| 6,711,532 B1 | 3/2004 | Spieksma |
| 6,893,874 B2 | 5/2005 | Stark |
| 7,560,711 B2 | 7/2009 | Hegazi |
| 2006/0043004 A1 | 3/2006 | Rose |

(Continued)

FOREIGN PATENT DOCUMENTS

| | | |
|---|---|---|
| CA | 27812723 A1 | 5/2014 |
| EP | 0794433 A1 | 9/1997 |

(Continued)

OTHER PUBLICATIONS

Igor N. Evdokimov & Alexandr R Losev, "Potential of UV-Visible Absorption Spectroscopy for Characterizing Crude Petroleum Oils," Oil and Gas Business (2007), 21 pages.

(Continued)

*Primary Examiner* — Lam Nguyen

(74) *Attorney, Agent, or Firm* — Abelman, Frayne & Schwab

(57) ABSTRACT

A system and a method for characterizing a crude oil sample from the weight and ultraviolet visible spectroscopy of the sample, including calculating a crude oil ultraviolet visible index and using the index to calculate the API gravity and the aromaticity of the sample.

18 Claims, 3 Drawing Sheets

(56) References Cited

U.S. PATENT DOCUMENTS

| | | |
|---|---|---|
| 2006/0047444 A1 | 3/2006 | Brown |
| 2006/0142955 A1 | 6/2006 | Jones |
| 2007/0295640 A1 | 12/2007 | Tan et al. |
| 2008/0037006 A1 | 2/2008 | Canas Triana |
| 2008/0253426 A1 | 10/2008 | Voelkening |
| 2009/0011517 A1 | 1/2009 | Hodges |
| 2009/0279072 A1 | 11/2009 | Arakawa |
| 2009/0290144 A1 | 11/2009 | Hegazi |
| 2009/0316139 A1 | 12/2009 | Shrestha |
| 2010/0113311 A1 | 5/2010 | Eccleston et al. |
| 2010/0211329 A1 | 8/2010 | Farquharson et al. |
| 2011/0152136 A1 | 6/2011 | Hughes et al. |
| 2014/0156241 A1 | 6/2014 | Kumar et al. |

FOREIGN PATENT DOCUMENTS

| | | |
|---|---|---|
| EP | 0552300 B1 | 7/1998 |
| EP | 0859236 A1 | 8/1998 |
| SU | 817486 A1 | 3/1981 |
| SU | 1523972 A1 | 11/1989 |

OTHER PUBLICATIONS

University of Oldenburg, Institute of Physics, "Catalogue of Optical Spectra of Oils," Jan. 2005, retrieved from http://las.physik.uni-oldenburg.de/data/spectra/index.htm, 6 pages.

K. Hidajat, et al., "Quality characterization of crude oils by partial least square calibration of NIR spectral profiles", Journal of Near Infrared Spectroscopy, vol. 8, 2000, p. 53-59.

\* cited by examiner

CHARACTERIZATION OF CRUDE OIL BY ULTRAVIOLET VISIBLE SPECTROSCOPY

RELATED APPLICATION

This application claims the benefit of U.S. Provisional Patent Application No. 61/445,217 filed Feb. 22, 2011, the disclosure of which is hereby incorporated by reference.

FIELD OF THE INVENTION

This invention relates to a method and process for the evaluation of samples of crude oil and its fractions by ultraviolet visible spectroscopy, avoiding the need to conduct crude oil assays.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

When produced at the well, crude oil is usually accompanied by variable amounts of sweet and sour gases, as well as formation brines having high total dissolved solids (TDS). The crude oil is usually stabilized and desalted soon after its production from a well.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

The yields, composition, physical and indicative properties of these crude oil fractions, where applicable, are then determined during the crude assay work-up calculations. Typical compositional and property information obtained in a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |

TABLE 2-continued

| Property | Unit | Property Type | Fraction |
|---|---|---|---|
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. The crude assay data help refiners to understand the general composition of the crude oil fractions and properties so that the fractions can be processed most efficiently and effectively in an appropriate refining unit.

In the field of organic chemistry, UV-visible spectrophotometry, which deals with electronic transitions within molecules, has traditionally provided unique information about aromatic and heteroaromatic compounds which absorb strongly in the UV region (200 nm-400 nm). Despite this and owing to the complex molecular nature of crude oil, UV-visible spectra of these oils are often described as featureless, poorly defined spectra. Specific individual aromatic compounds and components are known to have maxima at well-defined wavelengths.

If the wavelength maxima of known aromatic compounds and components are evaluated and extracted from the UV spectra of crude oils they can be used to formulate indices for the aromatic content of the crude oil. These indices can be related to other properties of the oil, e.g., API gravity, sulfur content, and other selected characteristics that define the quality and nature of the constituent products. Importantly, this information can be obtained relatively rapidly and inexpensively from a UV-visible scan as compared to the prior art assay methods described above.

Any new rapid, direct method to help better understand the crude oil composition and properties from the analysis of whole crude oil will save producers, marketers, refiners and/or other crude oil users substantial expense, effort and time. Therefore, a need exists for an improved system and method for determining the properties of crude oil fractions from different sources and classifying the crude oil fractions based on their boiling point characteristics and/or properties.

SUMMARY OF THE INVENTION

The above objects and further advantages are provided by the present invention which broadly comprehends a system and a method for characterizing samples of crude oil into grades by the index derived from the UV visible spectra and gravity. Applicant has found that if the wavelength maxima of known aromatic compounds and components are evaluated and extracted from the UV spectra of crude oils they can be used to formulate indices for the aromatic content of the crude oil. These indices can be related to other properties of the oil, e.g., API gravity, sulfur content, and other selected characteristics that define the quality and nature of the constituent products. Importantly, this information can be obtained relatively rapidly and inexpensively from a UV-visible scan as compared to the prior art assay methods described above.

In the method of the current invention, a crude oil ultraviolet visible index (which will be referred to for convenience as "CUVISI") is determined which serves as a basis for further calculations upon which the crude oil can be classified. API gravity or aromaticity is also estimated from the ultraviolet visible index. CUVISI or API gravity can be used to characterize the sample as extra heavy gravity, heavy gravity, medium gravity, light gravity, or super light gravity crude oil. Aromaticity, which is a measure of the percentage of the aromatic carbon atoms present in the sample, can also be used to characterize the compound type. The correlations will provide for the necessary characterization of the nature of crude oils without fractionation/distillation required for the crude oil assays. The method and system of the invention will enable producers, marketers and refiners to benchmark the oil quality and valuate the oil without performing the customary extensive and time-consuming crude oil assays.

BRIEF DESCRIPTION OF THE DRAWING

Further advantages and features of the present invention will become apparent from the following detailed description of the invention when considered with reference to the accompanying drawings, in which.

DETAILED DESCRIPTION OF INVENTION

Figure 1:
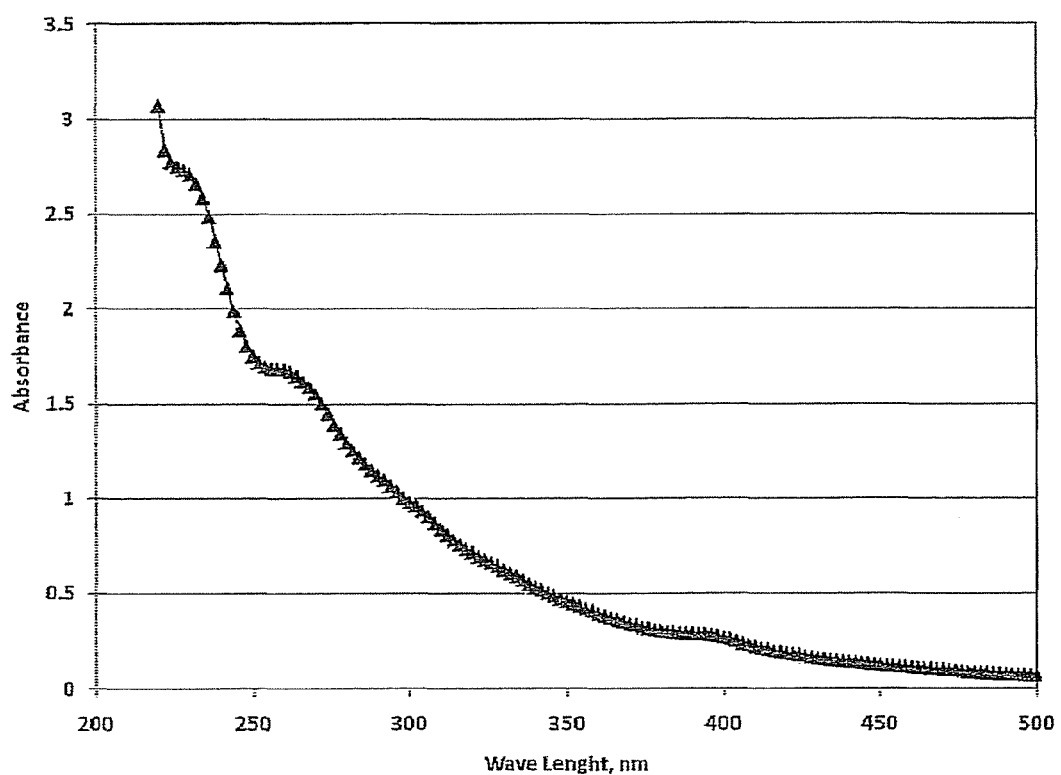
FIG. 1 is a graphic plot of typical ultraviolet visible spectroscopy data for a crude oil sample solution prepared as described below.
Figure 2:
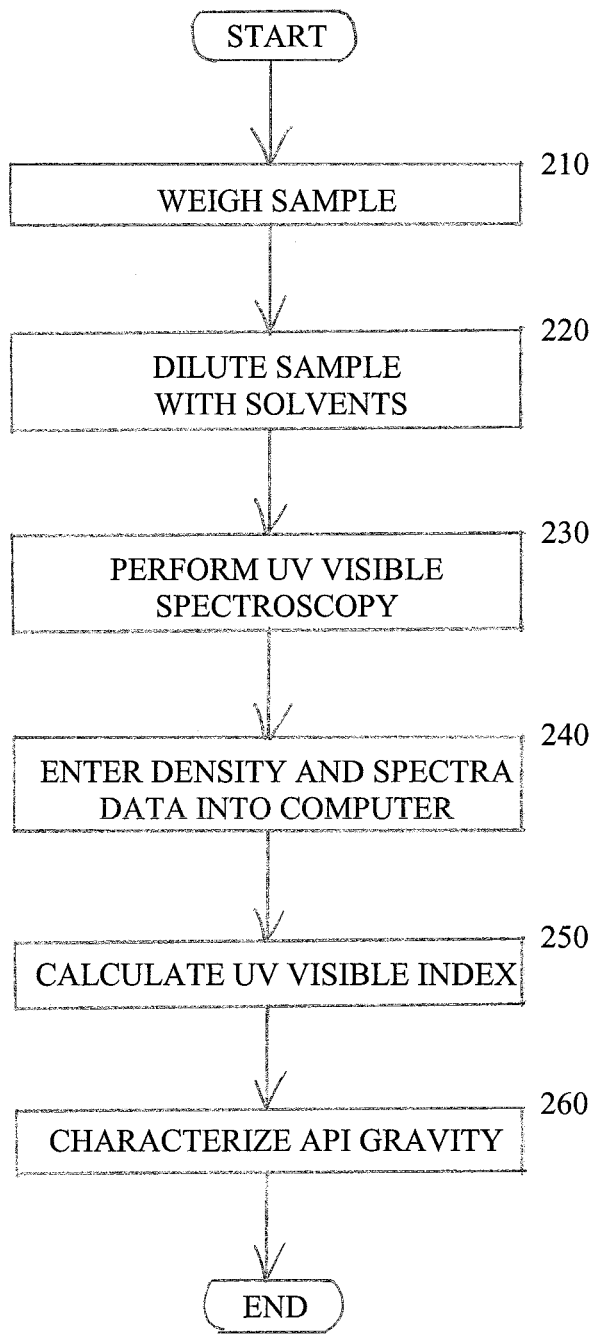
FIG. 2 is a process flow diagram of steps carried out to characterize the API gravity of a crude oil sample, using the system and method of the present invention.

FIG. 2 shows a process flowchart of steps that occur in one embodiment of the invention. Crude oil samples were prepared and analyzed by ultraviolet visible spectrophotometry between 200-500 nm, preferably 220-400 nm using a Jasco V-530 double beam spectrophotometer. In step 210, a crude oil sample is weighed.

In step 220, solutions were prepared by dissolving a milligram-sized sample of the crude oil in a two-part solvent system consisting of a paraffinic solvent having from 5-20 carbon atoms, preferred solvent being iso-octane, and a polar solvent, preferably, dichloromethane, at a ratio of 90:10% v/v. The polar solvents are selected based on their Hildebrand solubility factors or their two-dimensional solubility parameters. The overall Hildebrand solubility factor is a well known measure of polarity and has been calculated for numerous compounds. See, for example, the Journal of Paint Technology, Vol. 39, No. 505 (February 1967). The solvents can also be described by their two-dimensional solubility parameter. See, for example, I. A. Wiehe, "Polygon Mapping with Two-Dimensional Solubility Parameters", *I&EC Research*, 34, 661-673 (1995). The complexing solubility parameter component, which describes the hydrogen bonding and electron donor-acceptor interactions, measures the interaction energy that requires a specific orientation between an atom of one molecule and a second atom of a different molecule. The field force solubility parameter, which describes the van der Waals and dipole interactions, measures the interaction energy of the liquid that is not destroyed by changes in the orientation of the molecules.

The use of a polar solvent prevents precipitation of asphaltenes from the crude oil sample and ensures that all solutions are translucent for the measurement. The UV absorbance of the crude oil solutions is determined in a conventional one cm quartz cell. The absorbance values of the samples, normalized to 10 mg/L, are summed every even-numbered wavelength between 220 to 400 nm to calculate the characterization index.

In step 230, samples of a variety of crude oil in dilute solution were analyzed by UV-visible spectrophotometry over the wavelengths 220-400 nm. Dilute solutions were prepared by dissolving the oil in a two-part solvent system consisting of iso-octane (90 mL) and dichloromethane (10 mL). In a typical solution preparation, one drop (~6 mg±3 mg) of crude oil from a pre-weighed syringe is added to 100 mL of the solvent solution. The syringe is reweighed to determine the exact amount of the crude oil added. Each crude oil sample is analyzed at two concentration levels, e.g., 60 mg/L and 120 mg/L. Solutions are analyzed in 1 cm quartz cells using a Jasco V-530 double beam spectrophotometer.

The instrument is allowed to warm up for 30 minutes prior to analysis and is auto-zeroed without cells in both sample and reference beams. The reference cell is filled with the solvent mixture then placed in the reference beam. Solutions of the crude oil sample solutions prepared as described above are successively placed in a clean quartz sample cell and the spectra are recorded against the reference solvent blank. The spectra are recorded at a scan speed of 100 nm/min with a fast response time.

Table 3 is an example of a tabulation of values for the sample of Arab heavy crude oil in the wavelength range 220-400 nm. This data is depicted in the curve of the figure.

TABLE 3

Absorbances of Arab Heavy Crude Oils at Wavelength Ranging from 220-400 nm at 2 nm Interval

| Wave Length | Absor., nm |
|---|---|
| 220 | 3.076 |
| 222 | 2.841 |
| 224 | 2.778 |
| 226 | 2.753 |
| 228 | 2.735 |
| 230 | 2.708 |
| 232 | 2.663 |
| 234 | 2.591 |
| 236 | 2.486 |
| 238 | 2.361 |
| 240 | 2.236 |
| 242 | 2.113 |
| 244 | 1.994 |
| 246 | 1.891 |
| 248 | 1.811 |
| 250 | 1.755 |
| 252 | 1.719 |
| 254 | 1.698 |
| 256 | 1.689 |
| 258 | 1.688 |
| 260 | 1.685 |
| 262 | 1.673 |
| 264 | 1.649 |
| 266 | 1.621 |
| 268 | 1.59 |
| 270 | 1.552 |
| 272 | 1.502 |
| 274 | 1.447 |
| 276 | 1.39 |
| 278 | 1.341 |
| 280 | 1.297 |
| 282 | 1.255 |
| 284 | 1.218 |
| 286 | 1.183 |
| 288 | 1.15 |
| 290 | 1.121 |
| 292 | 1.096 |
| 294 | 1.067 |
| 296 | 1.036 |
| 298 | 1.006 |
| 300 | 0.981 |
| 302 | 0.962 |
| 304 | 0.935 |
| 306 | 0.905 |
| 308 | 0.871 |
| 310 | 0.839 |
| 312 | 0.809 |
| 314 | 0.783 |
| 316 | 0.758 |
| 318 | 0.735 |
| 320 | 0.714 |
| 322 | 0.696 |
| 324 | 0.678 |
| 326 | 0.662 |
| 328 | 0.645 |
| 330 | 0.627 |
| 332 | 0.609 |
| 334 | 0.59 |
| 336 | 0.57 |
| 338 | 0.551 |
| 340 | 0.532 |
| 342 | 0.518 |
| 344 | 0.502 |
| 346 | 0.486 |
| 348 | 0.472 |
| 350 | 0.458 |
| 352 | 0.445 |
| 354 | 0.432 |
| 356 | 0.418 |
| 358 | 0.406 |
| 360 | 0.394 |
| 362 | 0.382 |
| 364 | 0.37 |
| 366 | 0.359 |
| 368 | 0.349 |
| 370 | 0.34 |
| 372 | 0.332 |
| 374 | 0.323 |
| 376 | 0.316 |
| 378 | 0.309 |
| 380 | 0.303 |
| 382 | 0.299 |
| 384 | 0.294 |
| 386 | 0.292 |
| 388 | 0.29 |
| 390 | 0.289 |
| 392 | 0.288 |
| 394 | 0.287 |
| 396 | 0.283 |

TABLE 3-continued

Absorbances of Arab Heavy Crude Oils at Wavelength
Ranging from 220-400 nm at 2 nm Interval

| Wave Length | Absor., nm |
|---|---|
| 398 | 0.276 |
| 400 | 0.268 |

Equation (1) shows a crude oil ultraviolet visible index, CUVISI.

$$CUVISI = \sum_{i=220}^{310} (Absorbance_{(2i-220)}/x*10); \quad (1)$$

where:
Absorbance=absorbance value of the prepared crude oil sample solution at a specific wavelength over the range 220 nm to 400 nm at 2 nm intervals;
x=the weight of the sample used, in mg.

In step 240, the density and spectra data are entered into a computer. In step 250, the CUVISI is calculated.

In one embodiment, in step 260 the sample is then characterized as follows:
For CUVISI≥115, the sample is extra heavy gravity crude oil;
For 100≤CUVISI<115, the sample is heavy gravity crude oil;
For 80≤CUVISI<100, the sample is medium gravity crude oil;
For 50≤CUVISI<80, the sample is light gravity crude oil; and
For CUVISI<50, the sample is super light gravity crude oil.

The data recorded in Table 3 produces a CUVISI of 98.697. This classifies this crude oil as medium gravity crude oil.

In another embodiment, in step 270 the API gravity of the sample is derived from the CUVISI, and the API gravity can also be used to characterize the sample. The API gravity value is calculated in step 280 as follows:

$$API\ Gravity=-0.00176*CUVISI^2-0.00689*CUVISI+45.743 \quad (2).$$

The sample is then characterized as follows:
For API Gravity<20, the sample is extra heavy gravity crude oil;
For 20<API Gravity<27, the sample is heavy gravity crude oil;
For 27≤API Gravity<34, the sample is medium gravity crude oil;
For 34≤API Gravity<40, the sample is light gravity crude oil; and
For API Gravity≥40, the sample is super light gravity crude oil.

For the example provided in Table 3, for which CUVISI was determined to be 98.697, the API Gravity would be calculated as:
API Gravity=−0.00176*(98.697)$^2$−0.00689*(98.697)+45.743=27.9, which also identifies it as medium crude oil.

In another embodiment, the aromaticity of the sample can be derived from the CUVISI and used to further characterize the sample.

$$Aromaticity=-0.0000309999*CUVISI^2+0.127188*CUVISI+6.36006 \quad (3).$$

The sample is then characterized as follows:
For Aromaticity>10, the sample is aromatic;
For Aromaticity≤10, the sample is paraffinic/naphthenic.

The method is applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

Figure 3:
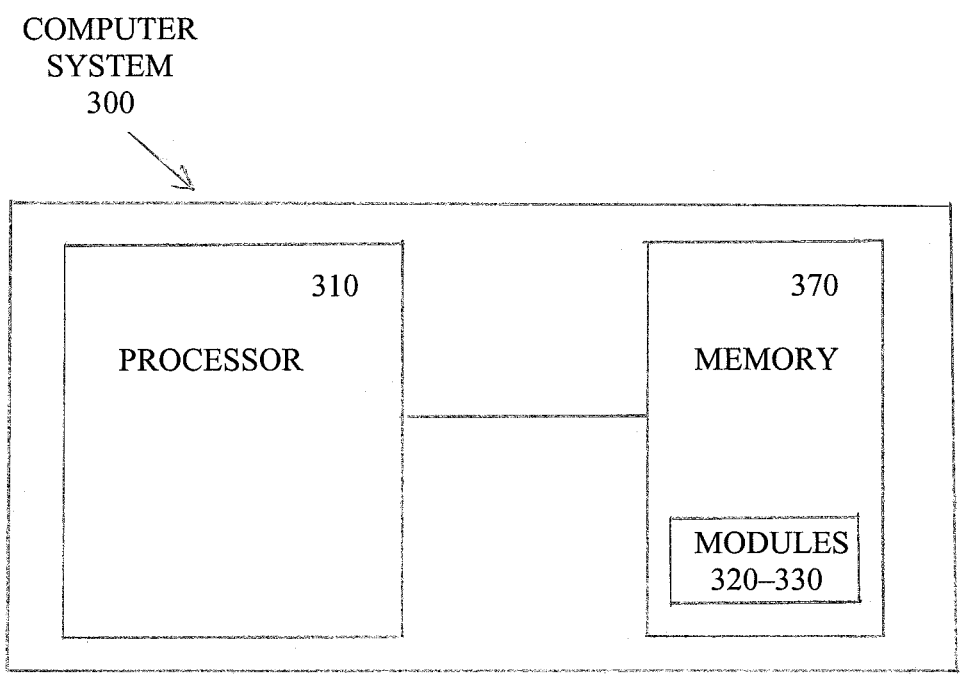
FIG. 3 is a block diagram of a component of a system for implementing the invention, according to one preferred embodiment of the present invention.

FIG. 3 illustrates an embodiment of the present invention, implemented in a computer system 300, with a number of modules. Computer system 300 includes a processor 310, and a memory unit 370. Memory unit 370 stores software program modules and associated data, and in particular stores a crude oil UV visible index (CUVISI) calculation module 320, and an API gravity characterization module 330 that performs its calculations based upon the CUVISI.

In an alternate embodiment, memory unit 370 stores a crude oil UV visible index (CUVISI) calculation module 320, an estimated API gravity calculation module 325, and an API gravity characterization module 330 that performs its calculations based upon the estimated API gravity.

The system and method of the present invention have been described above and with reference to the attached figure; however, modifications will be apparent to those of ordinary skill in the art and the scope of protection for the invention is to be defined by the claims that follow.

We claim:

1. A system for characterizing the API gravity of a sample of crude oil based upon ultraviolet visible spectroscopy data derived from the sample and the weight of the sample, the system comprising:
   an ultraviolet visible spectrophotometer;
   a non-volatile memory device that stores calculation modules and data;
   a processor coupled to the non-volatile memory;
   a first calculation module that calculates a crude oil ultraviolet visible index value for the sample from a summation of absorbance values of the spectroscopy data over a predetermined range of wavelengths, divided by the weight of the sample;
   and a second calculation module that characterizes the API gravity of the sample based on the crude oil ultraviolet visible index.

2. A system for characterizing the API gravity of a sample of crude oil based upon separately provided ultraviolet visible spectroscopy data of the sample and a separately provided weight of the sample, the system comprising:
   an ultraviolet visible spectrophotometer;
   a non-volatile memory device that stores calculation modules and data;
   a processor coupled to the non-volatile memory;
   a first calculation module that calculates a crude oil ultraviolet visible index of the sample from a summation of absorbance values of the spectroscopy data over a predetermined range of wavelengths, divided by the weight of the sample;
   a second calculation module that calculates an estimated API gravity of the sample based on the crude oil ultraviolet visible index;
   and a third calculation module that calculates a classification value for the sample from the estimated API gravity.

3. A method for operating a computer to characterize the API gravity of a sample of a hydrocarbon oil collected from an oil well, stabilizer, extractor, or distillation tower, the method comprising:

weighing the sample;
preparing the sample for ultraviolet visible spectroscopy analysis by diluting the sample with solvents;
obtaining ultraviolet visible spectroscopy data from an ultraviolet visible spectroscopy analysis in a wavelength range from 220-500 nm;
entering into the computer spectra data obtained by ultraviolet visible spectroscopy analysis of the sample;
calculating an ultraviolet visible index of the sample from a summation of absorbance values of the ultraviolet visible index spectroscopy data, divided by the weight of the sample;
calculating the API gravity of the sample from the ultraviolet visible index;
determining from the API gravity the nature of products that can be manufactured from the crude oil; and
determining an appropriate refining technology to allow the products to be processed most efficiently and effectively.

4. The method of claim 3, wherein the ultraviolet visible spectroscopy data is obtained from an ultraviolet visible spectroscopy analysis in a wavelength range from 220-400 nm.

5. The method of claim 3, wherein the solvent used is a mixture of paraffinic and polar solvents.

6. The method of claim 5, wherein the paraffinic solvent contains carbon from 5-20 atoms.

7. The method of claim 5, wherein the polar solvent is selected based on its Hildebrand solubility factor or by its two-dimensional solubility parameter.

8. The method of claim 7, wherein the polar solvent has a Hildebrand solubility rating of at least 19.

9. The method of claim 7, wherein the two-dimensional solubility factors of the polar solvent are the complexing solubility parameter and the field force solubility parameter.

10. The method of claim 9, wherein the polar solvent's complexing solubility parameter component describes the hydrogen bonding and electron donor acceptor interactions.

11. The method of claim 9, wherein the polar solvent's field force solubility parameter is based on the van der Waals and dipole interactions.

12. The method of claim 5, wherein the paraffinic-to-polar solvent ratio is 70:30 or greater.

13. The method of claim 5, wherein the paraffinic-to-polar solvent ratio is 90:10 or greater.

14. A method for operating a computer to characterize the API gravity of a sample of oil collected from an oil well, stabilizer, extractor, or distillation tower, the method comprising:
weighing the sample;
preparing the sample for ultraviolet visible spectroscopy analysis by diluting the sample with solvents;
obtaining spectra data for the sample by an ultraviolet visible spectroscopy analysis in a wavelength range from 220-500 nm;
entering into the computer the spectra data for the sample;
calculating an ultraviolet visible index of the sample based on a summation of absorbance values of the spectra data, divided by the weight of the sample;
calculating an estimated API gravity from the ultraviolet visible index;
classifying the sample from the estimated API gravity and determining from the API gravity the nature of products that can be manufactured from the crude oil; and
determining an appropriate refining technology to allow the products to be processed most efficiently and effectively.

15. The method of claim 14, wherein the ultraviolet visible spectroscopy data is obtained from an ultraviolet visible spectroscopy analysis in a wavelength range from 220-400 nm.

16. A system for characterizing a sample of crude oil based upon ultraviolet visible spectroscopy data for the sample and the weight of the sample, the system comprising:
an ultraviolet visible spectrophotometer;
a non-volatile memory that stores calculation modules and data;
a processor coupled to the non-volatile memory;
a first calculation module that calculates a crude oil ultraviolet visible index of the sample based on a summation of absorbance values of the spectroscopy data over a predetermined range of wavelengths, divided by the weight of the sample;
and a second calculation module that calculates the aromaticity of the sample from the crude oil ultraviolet visible index.

17. A system for characterizing a sample of crude oil based upon ultraviolet visible spectroscopy data for the sample and the weight of the sample, the system comprising:
an ultraviolet visible spectrophotometer;
a non-volatile memory that stores calculation modules and data;
a processor coupled to the non-volatile memory;
a first calculation module that calculates a crude oil ultraviolet visible index of the sample from a summation of absorbance values of the spectroscopy data over a predetermined range of wavelengths, divided by the weight of the sample;
a second calculation module that estimates the API gravity of the sample from the crude oil ultraviolet visible index;
and a third calculation module that calculates the aromaticity of the sample from the crude oil ultraviolet visible index.

18. A method for operating a computer to characterize a sample of crude hydrocarbon oil collected from an oil well, stabilizer, extractor, or distillation tower, the method comprising:
weighing the sample;
preparing the sample for ultraviolet visible spectroscopy analysis by diluting the sample with at least one paraffinic solvent and at least one polar solvent;
obtaining ultraviolet visible spectroscopic spectra data from an ultraviolet visible spectroscopy analysis in a wavelength range from 220-500 nm;
entering into the computer the spectra data obtained for the sample;
calculating an ultraviolet visible index of the sample based on a summation of absorbance values of the spectra data, divided by the weight of the sample;
characterizing the gravity of the sample from the ultraviolet visible index;
calculating the aromaticity of the sample from the ultraviolet visible index;
determining from the gravity and the aromaticity the nature of products that can be manufactured from the crude oil; and
determining an appropriate refining technology to allow the products to be processed most efficiently and effectively.

* * * * *